US012569582B2

(12) United States Patent
Wang et al.

(10) Patent No.: US 12,569,582 B2
(45) Date of Patent: Mar. 10, 2026

(54) LASER ASSISTED COLD PLASMA DISINFECTION DEVICE

(71) Applicants: Sean Xiaolu Wang, Wilmington, DE (US); Qun Li, Newark, DE (US)

(72) Inventors: Sean Xiaolu Wang, Wilmington, DE (US); Qun Li, Newark, DE (US)

(73) Assignee: B&W Tek, Inc., Newark, DE (US)

( * ) Notice: Subject to any disclaimer, the term of this patent is extended or adjusted under 35 U.S.C. 154(b) by 469 days.

(21) Appl. No.: 18/204,428

(22) Filed: Jun. 1, 2023

(65) Prior Publication Data

US 2023/0398248 A1      Dec. 14, 2023

Related U.S. Application Data

(60) Provisional application No. 63/404,566, filed on Sep. 8, 2022, provisional application No. 63/350,512, filed on Jun. 9, 2022.

(51) Int. Cl.
*A61L 2/14*        (2006.01)
*A61L 2/084*        (2026.01)
(52) U.S. Cl.
CPC ................. *A61L 2/14* (2013.01); *A61L 2/084* (2013.01)

(58) Field of Classification Search
CPC .......... A61L 2/14; A61L 2/084; A61L 2/0011; A61L 2/0052; A61L 2/0082; A61L 2/0094
See application file for complete search history.

(56) References Cited

U.S. PATENT DOCUMENTS

2020/0038530 A1*    2/2020    Yildirim .................. A61N 1/44

OTHER PUBLICATIONS

Wang et al. "Antimicrobial blue light inactivation of pathogenic microbes: State of the art." Drug Resistance Updates 33-35 (2017) 1-22. (Year: 2017).*

* cited by examiner

*Primary Examiner* — Timothy C Cleveland

(57) ABSTRACT

This invention discloses a laser assisted cold plasma device for overcoming the antimicrobial resistance and effectively killing the microbes. The microbes are first illuminated with laser light, which inactivates the antioxidant enzyme of the microbes and renders them susceptible to reactive oxygen species (ROS) attack. The microbes are then treated and killed with cold plasma. The synergy between the two treatments improves the effectiveness of microbe eradication by several orders of magnitude.

5 Claims, 2 Drawing Sheets

LASER ASSISTED COLD PLASMA DISINFECTION DEVICE

CROSS-REFERENCE TO RELATED APPLICATIONS

This application claims inventions which were disclosed in Provisional Patent Application No. 63/350,512, filed Jun. 9, 2022, entitled "ENHANCED COLD PLASMA DISINFECTION DEVICE" and Provisional Patent Application Ser. No. 63/404,566, filed Sep. 8, 2022, entitled "LASER ASSISTED COLD PLASMA DISINFECTION DEVICE". The benefit under 35 USC § 119(e) of the above-mentioned United States Provisional Applications is hereby claimed, and the aforementioned applications are hereby incorporated herein by reference.

FIELD OF THE INVENTION

This invention relates to a laser assisted cold plasma disinfection device.

BACKGROUND OF THE INVENTION

Antimicrobial resistance is an urgent global public health threat, killing at least 1.27 million people worldwide and associated with nearly 5 million deaths in 2019. In the U.S., more than 2.8 million antimicrobial-resistant infections occur each year. More than 35,000 people die as a result, according to CDC (Centers for Disease Control and Prevention)'s 2019 Antibiotic Resistance (AR) Threats Report. Approximately 80% of chronic and recurrent microbial infections in the human body are due to bacterial biofilm, which are clusters of bacteria that are attached to a surface and/or to each other and embedded in a self-produced matrix. Microbial cells within biofilms have shown 10-1000 times more antibiotics resistance than the planktonic cells.

Cold atmospheric-pressure plasma at or near room temperature generates numerous reactive oxygen species (ROS) and reactive nitrogen species (RNS), such as hydrogen peroxide ($H_2O_2$), singlet oxygen ($^1O_2$), superoxide anion ($O_2^-$), ozone ($O_3$), nitric oxide ($\cdot NO$), and hydroxyl radical ($\cdot OH$), as well as electrons, ions, and photons. Currently, cold plasma has been widely studied for bacterial inactivation and as therapy for infectious diseases. One challenge for cold plasma disinfection is that microbes have their own antioxidant enzymatic systems. One of the best known of these enzymes is superoxide dismutase (SOD), which catalyzes the breakdown of superoxide into hydrogen peroxide and water and is therefore a central regulator of ROS levels. Another well-known enzyme is catalase (CAT), which participates in cellular antioxidant defense by decomposing hydrogen peroxide, thereby preventing the generation of hydroxyl radicals by the Fenton reaction.

SUMMARY OF THE INVENTION

It is the overall goal of the present invention to provide a laser assisted cold plasma device for overcoming the antimicrobial resistance and effectively killing the microbes. The microbes are first illuminated with laser light, which inactivates the antioxidant enzyme of the microbes and renders them susceptible to reactive oxygen species (ROS) attack. The microbes are then treated and killed with cold plasma. The synergy between the two treatments improves the effectiveness of microbe eradication by several orders of magnitude.

BRIEF DESCRIPTION OF DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
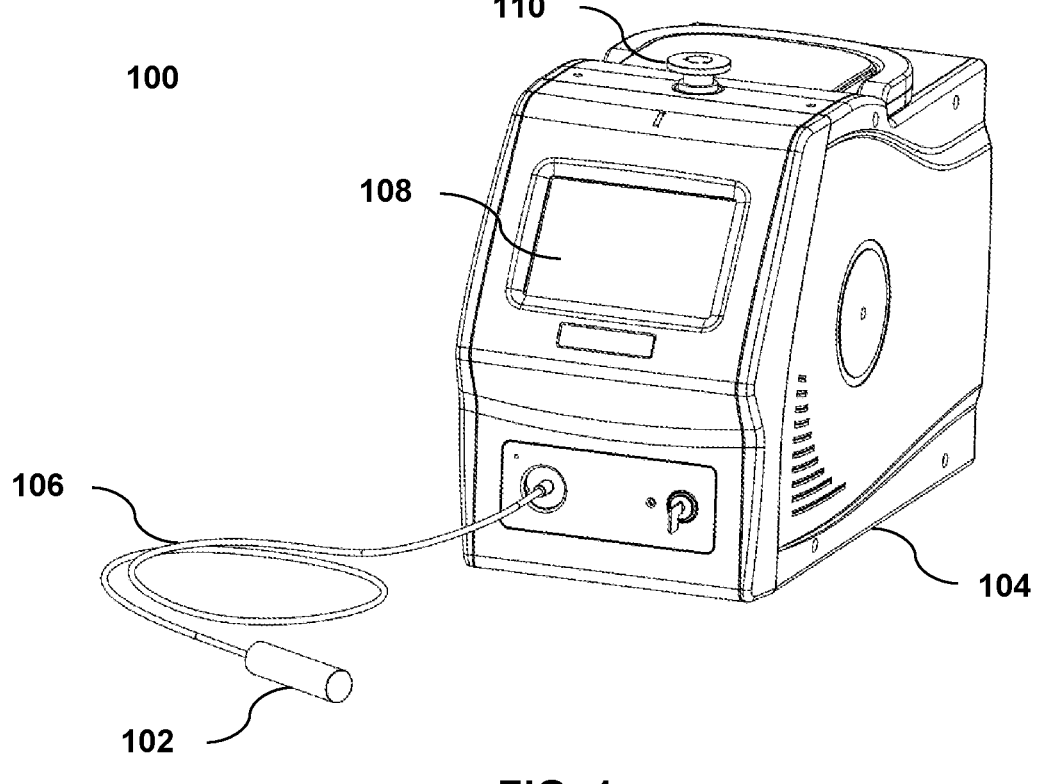
FIG. 1 illustrates one exemplary embodiment of the laser assisted cold plasma disinfection device.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Before describing in detail embodiments that are in accordance with the present invention, it should be observed that the embodiments reside primarily in combinations of method steps and apparatus components related to a laser assisted cold plasma disinfection device. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In one exemplary embodiment of the present invention as shown in FIG. 1, the laser assisted cold plasma disinfection device 100 comprises a dielectric barrier discharge (DBD) applicator 102, which is powered by a high voltage power supply 104 through a high voltage cable 106. Dielectric barrier discharge (DBD), which involves electrical discharge between two electrodes separated by an insulating dielectric barrier, is one effective method to produce cold plasma. For biomedical applications, the treatment subject is often employed as one of the electrodes, and the plasma discharge is produced between the dielectric barrier and the treatment subject. The power supply 104 is preferably a pulsed power supply with an adjustable repetition rate and output voltage. The output voltage is preferably in the range from 1 kV (kilovolt) to several tens of kV or even higher.

The power supply 104 comprises a touch screen 108 for the user to control the output voltage, repetition rate, duty cycle, and duration of the supplied power as well as for displaying the current values of these parameters. The power supply 104 further comprises an emergency switch 110 for shutting down the device in case of an emergency. The cold plasma disinfection device 100 is equipped with a laser or light emitting diode (LED) light source (not shown), which is embedded in the same enclosure of the high voltage power supply 104. The light source preferably emits violet/blue light in the wavelength range of 400-420 nm, which is delivered to the DBD applicator 102 via an optical fiber bundled together with the high voltage cable 106. The violet/blue light in this wavelength range can effectively inactivate catalase (CAT) residing inside microbes, subsequently rendering the microbes vulnerable to $H_2O_2$ and $H_2O_2$-producing agents. As the cold plasma generates a plurality of reactive oxygen species (ROS) including $H_2O_2$, the violet/blue light illumination will enhance the effectiveness of cold plasma for eradication of the microbes. The light source can be pulsed to provide high peak power yet maintain a low average power to minimize the adverse effect to the treatment subject.

Figures 2A, 2B:
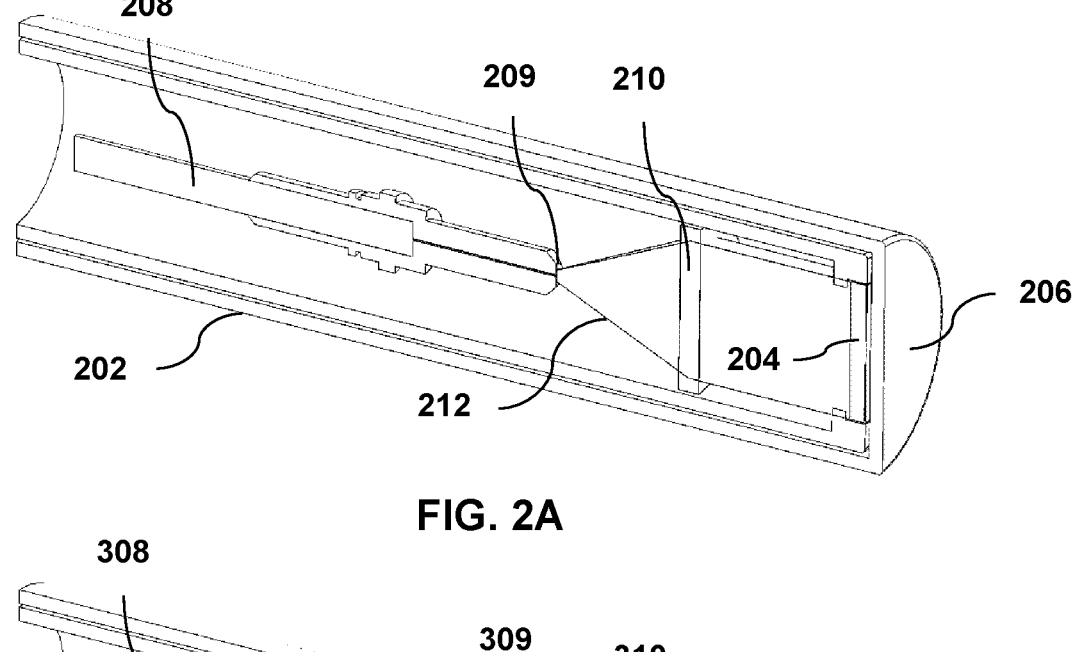
FIG. 2A illustrates one exemplary embodiment of the cold plasma applicator.
FIG. 2B illustrates another exemplary embodiment of the cold plasma applicator.

Two exemplary embodiments of the DBD applicator of the present invention are shown in FIG. 2A and FIG. 2B, respectively. In FIG. 2A, the DBD applicator 202 comprises an electrode 204 made of an optically transparent material (e.g., indium tin oxide (ITO)) and an optically transparent dielectric barrier 206 (e.g., quartz). When a high voltage is supplied from the power supply to the transparent electrode 204, cold plasma is generated between the treatment subject (not shown) and the dielectric barrier 206. The violet/blue light from the light source is delivered from the light source to the DBD applicator 202 via optical fiber 208, which is then collected by an optical lens 210 to output through the transparent electrode 204 and the transparent dielectric barrier 206. The violet/blue light illuminates the subject either before or during cold plasma treatment for inactivation of catalase (CAT) in the microbes. The reactive oxygen species (ROS) produced by the cold plasma then kills the microbes. The distance between the output end 209 of the optical fiber 208 and the optical lens 210 can be adjusted such that the beam size of the output violet/blue light can be adaptively controlled to match with the size of the treatment site. This design ensures that only the treatment site is illuminated by the violet/blue light. Hence the synergy of violet/blue light and cold plasma treatment only applies to the treatment site to minimize possible adverse effects to adjacent healthy tissues.

In FIG. 2B, the DBD applicator 302 comprises a meshed metal (e.g., copper) electrode 304 and an optically transparent dielectric barrier 306. When a high voltage is supplied from the power supply to the meshed metal electrode 304, cold plasma is generated between the treatment subject (not shown) and the dielectric barrier 306. The violet/blue light from the light source is delivered from the light source to the DBD applicator 302 via optical fiber 308, which is then collected by an optical lens 310 to output through the meshes of the meshed metal electrode 304 and the transparent dielectric barrier 306. The distance between the output end 309 of the optical fiber 308 and the optical lens 310 can be adjusted such that the beam size of the output violet/blue light can be adaptively controlled to match with the size of the treatment site.

As another feature of the present invention, the Raman scattering signal generated by the violet/blue light can be utilized for monitoring the status of the microbes under the combined violet/blue light and cold plasma treatment. As the wavelength of the violet/blue light falls on the absorption peak of catalase (CAT), there is a potential that the Raman scattering signal of catalase being amplified through resonant Raman effect, making it easier to be detected from the fluorescence background. A customized fiber optic Raman probe can be designed to fit into the DBD applicator for collecting the Raman scattering signal of the microbes during violet/blue light illumination. Changes in catalase (CAT) activity can be monitored by measuring the intensity variation of the related Raman peaks such as 754 $cm^{-1}$ and 1200 $cm^{-1}$ to 1500 $cm^{-1}$.

The laser assisted cold plasma disinfection device 100 may further comprise additional light sources emitting at wavelengths falling on the absorption bands of superoxide dismutase (SOD) (e.g., at around 470 nm and 660 nm) for the inactivation of SOD. As cold plasma produces a plurality of reactive oxygen species (ROS) in addition to $H_2O_2$ and SOD is the key antioxidant enzyme residing inside microbes which catalyzes the breakdown of superoxide, the inclusion of these wavelengths will further improve the effectiveness of the cold plasma disinfection device.

The laser assisted cold plasma disinfection device is a non-pharma energy device and is effective in drug-resistance bacteria/fungus elimination. Wavelength of the light used is in the visible range to avoid UV damage. This particular wavelength of violet/blue light is used in several FDA (U.S. Food and Drug Administration) cleared applications including teeth whitening, cosmetic and medical dermatology treatment and as such is deemed to be safe. Cold plasma treatments are demonstrated to be well-tolerated by skin and do not damage the skin barrier nor cause skin dryness. Hence the laser assisted cold plasma disinfection device is a low-risk medical device. The regulatory clearance and approval is straightforward for expedited entry into the market.

As another variation of the present invention, the laser/LED light can be combined with a non-equilibrium atmospheric pressure plasma jet (APPJ) device, in which the laser light shares the same pathway of the gas flow of the APPJ device. The laser/LED light inactivates the antioxidant enzyme in the microbes. The cold plasma provided by the APPJ device then kills the microbes.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The invention claimed is:

1. An apparatus for overcoming antimicrobial resistance and effectively killing microbes, the apparatus comprising:
   a light source producing light illuminating the microbes,
      wherein the light inactivates antioxidant enzyme of the microbes and renders the microbes susceptible to reactive oxygen species (ROS) attack; and

a dielectric barrier discharge (DBD) plasma device pro-
ducing cold plasma containing reactive oxygen species
(ROS), wherein the cold plasma is applied to the
microbes for killing the microbes;
wherein the dielectric barrier discharge (DBD) plasma
device comprises an optically transparent dielectric
barrier and an electrode made of an optically transpar-
ent material, wherein the light transmits through the
transparent electrode and the transparent dielectric bar-
rier to illuminate the microbes.

2. The apparatus of claim 1, wherein the light source is a
laser light source.

3. The apparatus of claim 1, wherein the light source is a
light emitting diode (LED) light source.

4. The apparatus of claim 1, wherein the light source
produces light having a wavelength in the range of 400-420
nm for the inactivation of catalase (CAT) in the microbes.

5. The apparatus of claim 1, wherein the light source
produces light having a wavelength at around 470 nm or at
around 660 nm for the inactivation of superoxide dismutase
(SOD) in the microbes.

\* \* \* \* \*

6